United States Patent [19]

Balasubramanyan et al.

[11] 4,079,143
[45] Mar. 14, 1978

[54] FUNGICIDAL 1H-1,2,4-TRIAZOLES

[75] Inventors: Sugavanam Balasubramanyan, Wokingham; Margaret Claire Shephard, Maidenhead, both of England

[73] Assignee: Imperial Chemical Industries Limited, London, England

[21] Appl. No.: 718,207

[22] Filed: Aug. 26, 1976

[30] Foreign Application Priority Data

Aug. 26, 1975  United Kingdom ............... 35208/75
Sep. 10, 1975  United Kingdom ............... 37241/75
Jul. 2, 1976   United Kingdom ............... 27649/76

[51] Int. Cl.² ............................................. A01N 9/00
[52] U.S. Cl. ............................. 424/269; 260/308 R; 542/429; 542/400
[58] Field of Search ................ 260/308 R; 424/269

[56] References Cited

U.S. PATENT DOCUMENTS

| 3,658,813 | 4/1972 | Godefroi et al. ............... 260/240 K |
| 3,872,117 | 3/1975 | Meiser et al. ................. 260/247.2 B |
| 3,912,752 | 10/1975 | Meiser et al. ................. 260/308 R |
| 3,952,002 | 4/1976 | Kramer et al. ................. 260/308 R |

FOREIGN PATENT DOCUMENTS

| 2,431,407 | 8/1973 | Germany. |
| 754,111 | 4/1976 | South Africa. |
| 1,244,530 | 9/1971 | United Kingdom. |
| 1,364,952 | 8/1974 | United Kingdom. |

OTHER PUBLICATIONS

Ainsworth et al. - C.A. 50, 1785 def (1956).
Leonardi et al. - C.A. 83, 97150y (1975).

*Primary Examiner*—Raymond V. Rush
*Attorney, Agent, or Firm*—Cushman, Darby & Cushman

[57] ABSTRACT

Plant fungicidal compounds of formula:

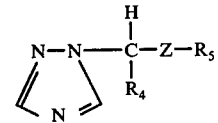

wherein $R_4$ is hydrogen, $C_{1-6}$ alkyl, alkenyl or alkynyl having up to 4 carbon atoms, phenyl or optionally ring-substituted benzyl or α-($C_{1-4}$ alkyl)-benzyl, $R_5$ is hydroxy, $C_{1-6}$ alkyl or alkoxy, amino, hydrazino, ($C_{1-6}$ alkyl) amino, benzylamino, benzyloxy, cycloalkoxy, cycloalkyl, optionally ring-substituted phenylamino or optionally substituted phenyloxy, Z is C = O or a derivative thereof, or a salt of such a compound.

1 Claim, No Drawings

FUNGICIDAL 1H-1,2,4-TRIAZOLES

This invention relates to heterocyclic compounds which are 1,2,4-triazole compounds, to compositions containing them and to methods of combating pests (particularly fungal pests) using them.

The compounds have the general formula (I):

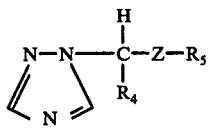

wherein $R_4$ is hydrogen, $C_{1-6}$ alkyl, alkenyl or alkynyl having up to 4 carbon atoms, phenylallyl, phenyl, benzyl optionally ring-substituted with for example halogen, $C_{1-4}$ alkyl or alkoxy, nitro, trifluoromethyl, cyano or methylenedioxy, or α-($C_{1-4}$ alkyl) benzyl optionally ring-substituted with for example halogen, and $R_5$ is hydroxy, $C_{1-6}$ alkyl or alkoxy, amino, hydrazino, phenylamino optionally ring-substituted with for example $C_{1-4}$ alkyl, halogen, nitro or trifluoromethyl, ($C_{1-6}$ alkyl) amino, phenyloxy optionally substituted with for example halogen, benzylamino, benzyloxy, cycloalkoxy or cycloalkyl; and Z is C = O or a derivative thereof; or a salt of such a compound.

The compounds can contain chiral centre(s). Normally the compounds are prepared in the form of racemic mixtures. However these and other mixtures can be separated into the individual isomers by methods known in the art.

The halogen can be fluorine, chlorine, bromine or iodine while the alkyl group can be one of the groups listed below for $R_4$.

The phenyl group can be substituted by halogen, alkyl, nitro, trifluoromethyl, cyano, alkoxy or alkylenedioxy (e.g. methylenedioxy).

Suitable C = O derivatives are ketals, hydrazones, semicarbazones, imines and oximes.

Examples of suitable $R_4$ groups are methyl, ethyl, propyl (n- or i-propyl), butyl (n-, i- or t-butyl), amyl (e.g. isopentyl), hexyl (e.g. 3,3-dimethylbutyl), heptyl, allyl, propynyl (e.g. propargyl), phenyl, tolyl (e.g. m-tolyl), 3-phenylallyl, benzyl, 2-, 3-or 4-fluorobenzyl, 4-chlorobenzyl, 2-bromobenzyl-, 3,4-, 2,6- or 2,4-dichlorobenzyl, α-methylbenzyl, 4-cyanobenzyl, 2-, 3- or 4-nitrobenzyl, 3-methylbenzyl, α-methyl-4-chlorobenzyl, 3-trifluoromethylbenzyl, 3-nitro-4-chlorobenzyl, 2-methoxy-5-nitrobenzyl or 2-chloro-4,5-methylenedioxybenzyl.

$R_5$ can be one of the alkyl and benzyl groups listed above for $R_4$ chain alkyl. Examples of suitable cycloalkyl groups are cyclohexyl and cyclopentyl. Other suitable $R_5$ groups are methoxy, ethoxy, propoxy (e.g. i-propoxy), butoxy (e.g. n- or t-butoxy), allyloxy, —OC(CH$_3$)$_2$C$_2$H$_5$, —OCH$_2$C(CH$_3$)$_3$, O(CH$_2$)$_2$C(CH$_3$)$_3$, benzyloxy, cyclopentyloxy, phenoxy or p-chlorophenoxy. Further examples of suitable $R_5$ groups are phenylamino, n- or t-butylamino, 1,1- or 2,2-dimethylpropylamino, amino, hydrazino, benzylamino, o- or p-chlorophenylamino, p-tolylamino, m-chloro-p-tolylamino, p-nitrophenylamino, —NHCH$_2$C(CH$_3$)$_3$, m-chloro-p-nitrophenylamino, or m-trifluoromethylphenylamino.

The salts of the compounds can be salts of organic or inorganic acids e.g. hydrochloric, sulphuric, acetic or oxalic acid, or, when $R_5$ is hydroxy, salts with alkali metals, for example lithium, sodium or potassium, alkaline earth metals, for example calcium and magnesium, ammonia and primary, secondary or tertiary amines, for example mono-, di- or tri- ($C_{1-6}$ aliphatic) amines.

Examples of suitable triazole compounds are shown in Table I.

TABLE I

| COMPOUND NO | $R_4$ | $R_5$ | Z | MELTING (OR BOILING) POINT ° C |
|---|---|---|---|---|
| 1 | H | t-Bu | C=O | 63–5° |
| 2 | H | OMe | C=NH | (126° /0.1 mm) |
| 3 | n-Bu | OH | C=O | 88–89° |
| 4 | i-Pr | OEt | C=O | (78–80° /0.1 mm) |
| 5 | n-Bu | NHPh | C=O | 110–111° |
| 6 | n-Bu | NH-n-Bu | C=O | Thick Oil* |
| 7 | n-Bu | O-t-Bu | C=O | (120° /0.1 mm) |
| 8 | n-Bu | NH$_2$ | C=O | 121–123° |
| 9 | n-Bu | O-⟨C$_6$H$_4$⟩-Cl | C=O | Thick Oil* (99%) |
| 10 | —CH$_2$-⟨C$_6$H$_4$⟩-Cl | t-Bu | C=O | 122–123° |
| 11 | i-Pr | NHNH$_2$ | C=O | 123–125° |
| 12 | CH$_2$CH=CH$_2$ | t-Bu | C=O | (130° /0.1 mm) |
| 13 | n-Bu | NHCH$_2$Ph | C=O | Thick Oil* |
| 14 | n-Bu | NH-⟨C$_6$H$_4$⟩-CH$_3$ | C=O | 124–126° |
| 15 | CH$_2$Ph | t-Bu | C=O | 69–70° |
| 16 | n-Bu | OCH$_2$Ph | C=O | (140° /0.1 mm) |

TABLE I-continued
| COMPOUND NO | R₄ | R₅ | Z | MELTING (OR BOILING) POINT ° C |
|---|---|---|---|---|
| 17 | 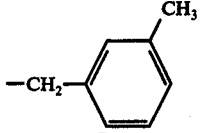 | t-Bu | C=O | 64–66° |
| 18 | n-Bu | 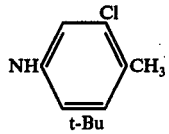 | C=O | 85–87° |
| 19 |  | t-Bu | C=O | 140–2° |
| 20 | i-Pr | 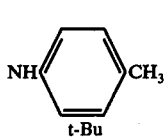 | C=O | 96–98° |
| 21 | 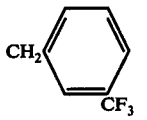 | t-Bu | C=O | 68–70° |
| 22 | n-Bu | 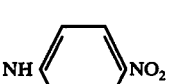 | C=O | 164–166° |
| 23 | n-Bu | O-n-Bu | C=O | (104–106° /.06 mm) |
| 24 | n-Bu | O-i-Pr | C=O | (94–96° /.07 mm) |
| 25 | n-Bu |  | C=O | (130–132° /.06 mm) |
| 26 | Ph | NH-n-Bu | C=O | Oil* (not pure) |
| 27 | 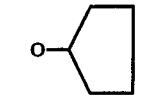 | t-Bu | C=O | |
| 28 |  | t-Bu | C=O | 85–86° |
| 29 |  | t-Bu | C=O | 122–125° |
| 30 | n-Bu | NH—t—Bu | C=O | 65–67° |
| 31 | n-Bu | t-Bu | C=O | 94–96° |
| 32 | Ph | 0-t-Bu | C=O | 79–82° |
| 33 | H | NH₂ | C=O | 180° |
| 34 | CH₂.C≡CH | t-Bu | C=O | 83–85° |
| 35 | 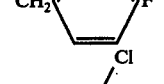 | t-Bu | C=O | 84–86° |
| 36 |  | t-Bu | C=O | 88–89° |
| 37 |  | t-Bu | C=O | 130–132° |
| 38 | i-Bu | NH-t-Bu | C=O | 127–129° |

TABLE I-continued

| COMPOUND NO | R₄ | R₅ | Z | MELTING (OR BOILING) POINT °C |
|---|---|---|---|---|
| 39 | (CH₂)₂CH(CH₃)₃ | NH—C₆H₄—Cl | C=O | 119–121° |
| 40 | n-Bu | NH.CH₂.C(CH₃)₃ | C=O | Waxy solid* |
| 41 | i-Bu | OC(CH₃)₂C₂H₅ | C=O | (70–80°/.15 mm) |
| 42 | i-Bu | O-t-Bu | C=O | (70–80°/.2 mm) |
| 43 | Ph | NH-t-Bu | C=O | 124–126° |
| 44 | n-Bu | O.CH₂.C(CH₃)₃ | C=O | (106–108°/.08 mm) |
| 45 | Me | NH—C₆H₄—Cl | C=O | 161–163° |
| 46 | i-Bu | NH-n-Bu | C=O | Oil* |
| 47 | Me | NH-t-Bu | C=O | 92–94° |
| 48 | Me | O-t-Bu | C=O | (~100°/20 mm) |
| 49 | CH₂—C₆H₃(Cl)(Cl) | t-Bu | C=O | 140–142° |
| 50 | CH₂—C₆H₄—Cl | i-Pr | C=O | 115–117° |
| 51 | CH₂—C₆H₃(MeO)(NO₂) | t-Bu | C=O | 185–187° |
| 52 | CH₂Ph | i-Pr | C=O | 83–84° |
| 53 | CH₂—C₆H₄—Br | t-Bu | C=O | 76–77° |
| 54 | CH₂—C₆H₃(NO₂)(Cl) | t-Bu | C=O | 100–102° |
| 55 | CH₂.CH=CHPh | t-Bu | C=O | 49–50° |
| 56 | CH₂—C₆H₂(Cl)(OC₂H₅)(O) | t-Bu | C=O | 127–129° |
| 57 | CH(CH₃)Ph | t-Bu | C=O | 86–89° |
| 58 | n-Bu | NH—C₆H₃(Cl)(NO₂) | C=O | 96–98° |
| 59 | n-Bu | NH—C₆H₄—Cl | C=O | Oil* |
| 60 | n-Bu | NH—C₆H₄—CF₃ | C=O | 104–106° |
| 61 | n-Bu | NHC(CH₃)(C₂H₅)(CH₃) | C=O | Oil* |

TABLE I-continued

| COMPOUND NO | R₄ | R₅ | Z | MELTING (OR BOILING) POINT ° C |
|---|---|---|---|---|
| 62 | CH₂—C₆H₄—NO₂ | i-Pr | C=O | 121–123° |
| 63 | CH₂—C₆H₄—F | i-Pr | C=O | 71–74° |
| 64 | CH₂—C₆H₄—CN | i-Pr | C=O | 117–119° |
| 65 | CH₂—C₆H₃(Cl)—Cl | i-Pr | C=O | 78–80° |
| 66 | CH₂—C₆H₄—Cl | 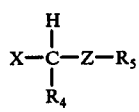 | C=O | 80–82° |
| 67 | CH(CH₃)—C₆H₄—Cl | t-Bu | C=O | 143–146° |
| 68 | i-Pr | NH—C₆H₄—NO₂ 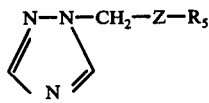 | C=O | 200–202° |

*The indicated structures of these compounds were confirmed by NMR and mass spectrographic analysis.

The compounds may be made by reacting 1,2,4-triazole or a salt thereof with the appropriate activated halo compound (for example an α-haloketone, α-haloacid, α-haloester, α-haloamide or substituted alkyl halide) using methods set out in the literature. Thus 1,2,4-triazole, or a salt thereof, can be reacted with a compound of general formula (II):

$$X-\underset{R_4}{\underset{|}{\overset{H}{\overset{|}{C}}}}-Z-R_5$$

wherein X is halogen, preferably bromine or chlorine, and $R_4$, $R_5$ and Z are as defined above.

Alternatively, the compounds wherein $R_4$ is other than hydrogen can be made by hydrocarbylating (e.g. with an appropriately substituted alkylating or aralkylating agent) a compound of general formula (III);

$$\underset{N}{\overset{N-N-CH_2-Z-R_5}{\diagdown\!\diagup}}$$

wherein Z, and $R_5$ are as defined above, or a salt thereof, suitably in the presence of a base in a hydroxylic or non-hydroxylic solvent using methods set out in the literature.

These processes may in some cases be carried out by heating the reactants together in the absence of a solvent or diluent, but preferably a solvent is present. Suitable solvents are non-hydroxylic solvents such as acetonitrile (which is preferred), dimethylformamide, dimethyl sulphoxide, sulpholane and tetrahydrofuran. Hydroxylated solvents, for example methanol and ethanol, may be used in certain circumstances when the presence of the hydroxyl group does not interfere with the progress of the reaction. The processes may also be carried out in the presence of a base, but preferably excess triazole is present to remove liberated HX from the reaction. Other suitable bases are sodium hydride (although not when a hydroxylated solvent or diluent is used), alkali metal carbonates (such as potassium carbonate) and alkali metal hydroxides (such as potassium hydroxide). The reaction temperature depends upon the choice of reactants, solvent and base, but generally the reaction mixture is refluxed.

The processes generally involve dissolving the reactants in a solvent and, after allowing reaction to occur, isolating the product by removal of the reactant solvent in vacuo.

The unreacted triazole is removed by extraction of the product with a suitable solvent and the extract is washed with water. A crystallisation or other purification procedure may then be carried out if desired.

The activated halo compounds may be made by any of the methods set out in the literature.

The compounds wherein Z is a derivative of C = O may be made from the respective carbonyl compound using any of the standard techniques set out in the literature.

The compounds are active fungicides, particularly against the following diseases:

*Piricularia oryzae* on rice

*Puccinia recondita* and other rusts on wheat and rusts on other hosts

*Plasmopara viticola* on vines

*Erysiphe graminis* (powdery mildew) on barley and wheat and other powdery mildews on various hosts such as *Sphaerotheca fulginea* on cucumbers, *Podosphaera leucotricha* on apples and *Uncinula necator* on vines

*Botrytis cinerea* (grey mould) on tomatoes, strawberries, vines and other hosts

*Gleosporiun musarum* on bananas and *Penicillium digitatum* on oranges (Compounds 8 and 19 show activity against these latter two)

Some of the compounds are active in the form of seed dressings against:

*Fusarium* spp., *Septoria* ssp., *Tilletia* ssp., and *Pyrenophora* spp. on cereals.

The compounds also have certain anti-bacterial and anti-viral activities.

They may be used as such for anti-fungal purposes but are more conveniently formulated into compositions for such usage.

The invention therefore also provides a fungicidal composition comprising, as an active ingredient, a triazole compound or salt thereof, and a carrier for the active ingredient.

The invention also provides a method for combating pests, which are fungi, viruses or bacteria, which method comprises treating plants, seeds or trees with a triazole compound or salt thereof as hereinbefore defined.

The compounds can be used to combat plant pests and treat plants or seeds in a number of ways, for example they can be applied, formulated or unformulated, directly to the foliage of a plant which is infected or likely to become infected, or they can be applied also to bushes and trees, to seeds or to other medium in which plants, bushes or trees are growing or are to be planted, or they can be sprayed on, dusted on or applied as a cream or paste formulation. Application can be to any part of the plant, bush or tree, for example to the foliage, stems, branches or roots, or to soil surrounding the roots.

The term "treating" as used herein refers to all these modes of application and the term "plant" includes seedlings, bushes and trees. Furthermore, the method of the invention includes preventative, protectant, prophylactic and eradicant treatment.

The compounds are preferably used for agricultural and horticultural purposes in the form of a composition. The type of composition used in any instance will depend upon the particular purpose envisaged.

The compositions may be in the form of dusting powders or granules comprising the active ingredient and a solid diluent or carrier, for example, kaolin, bentonite, kieselguhr, dolomite, calcium carbonate, talc, powdered magnesia, Fuller's earth, gypsum, Hewitt's earth, diatomaceous earth and China clay. Compositions for dressing seed, for example, may comprise an agent (for example a mineral oil) for assisting the adhesion of the composition to the seed.

The compositions may also be in the form of dispersible powders or grains comprising a wetting agent to facilitate the dispersion in liquids of the powder or grains which may contain also fillers and suspending agents.

The aqueous dispersions or emulsions may be prepared by dissolving the active ingredient(s) in an organic solvent optionally containing wetting, dispersing or emulsifying agent(s) and then adding the mixture to water which may also contain wetting, dispersing or emulsifying agent(s). Suitable solvents are ethylene dichloride, isopropyl alcohol, propylene glycol, diacetone alcohol, toluene, kerosene, methylnaphthalene, the xylenes and trichloroethylene.

The compositions to be used as sprays may also be in the form of aerosols wherein the formulation is held in a container under pressure in the presence of a propellant, e.g. fluorotrichloromethane or dichlorodifluoromethane.

By including suitable additives, for example additives for improving the distribution, adhesive power and resistance to rain on treated surfaces, the different compositions can be better adapted for various utilities.

The compounds can be used as mixtures with fertilisers (e.g. nitrogen- or phosphorous-containing fertilisers). Compositions comprising only granules of fertiliser incorporating, for example coated with, the triazole compound are preferred. The invention therefore also provides a fertiliser composition comprising the triazole compound.

The compositions may also be in the form of liquid preparations for use as dips or sprays which are generally aqueous dispersions or emulsions containing the active ingredient in the presence of one or more wetting agent(s), dispersing agent(s), emulsifying agent(s) or suspending agent(s). These agents can be cationic, anionic or non-anionic agents.

Suitable cationic agents are quaternary ammonium compounds for example, cetyltrimethylammonium bromide. Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropyl-naphthalene sulphonates). Suitable non-ionic agents are the condensation products of ethylene oxide with fatty alcohols such as oleyl alcohol or cetyl alcohol, or with alkyl phenols such as octylphenol, nonylphenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersions or emulsions are generally supplied in the form of a concentrate containing a high proportion of the active ingredient(s), the concentrate to be diluted with water before use. These concentrates often should be able to withstand storage for prolonged periods and after such storage be capable of dilution with water in order to form aqueous preparations which remain homogeneous for a sufficient time to enable them to be applied by conventional spray equipment. The concentrates may conveniently contain 10–85%, generally 25–60%, by weight of the active ingredient(s). When diluted to form aqueous preparations, such preparations may contain varying amounts of the active ingredient(s) depending upon the intended purpose, but an aqueous preparation containing 0.0005% or 0.01 to 10% by weight of active ingredient(s) may be used.

The compositions of this invention can comprise also other compound(s) having biological activity, as well as stabilising agent(s), for example epoxides (e.g. epichlorhydrin).

The following Examples illustrate the invention; the temperatures are given in degrees Centigrade (° C).

EXAMPLE 1

α-1,2,4-Triazol-1-yl-pinacolone (Compound 1)

1,2,4-Triazole (33.4 g) and sodium ethoxide [from sodium (11.6 g) and ethyl alcohol (250 ml)] were refluxed for 1 hour. To this solution at the reflux temperature was added bromopinacolone (87 g), and the mixture was then heated for 2 hours. It was then cooled to ambient temperature and filtered to remove the precipitated sodium bromide; the solvent was removed in vacuo. The residue was extracted with chloroform (100 ml). The extract was washed with water (4 × 15 ml), dried (sodium sulphate) and filtered. Petroleum ether (50 ml; b.p. 60°–80°) was added and the solution concentrated to give α-1,2,4-triazol-4-yl-pinacolone, m.p. 176°. Further concentration of the solution gave the title compound, m.p. 63°–65°.

EXAMPLE 2

1-Imino-2-(1,2,4-triazol-1-yl)ethyl Methyl Ether (Compound 2)

1,2,4-Triazole (3.45 g) was added to a sodium methoxide in methanol [prepared from sodium (1.15 g) and methanol (40 ml)], and the mixture was refluxed for 1 hour, and cooled to 25° C; chloroacetonitrile (3.78 g) was then added and the mixture was refluxed for a further 6 hours. The solution was filtered and the solvent removed in vacuo. The resultant mixture was dissolved in petroleum ether (50 ml; b.p. 40°–60° C) and the solution filtered to remove unreacted 1,2,4-triazole. Removal of the solvent in vacuo gave a residue which on distillation gave the title compound.

EXAMPLE 3

Ethyl α-1,2,4-triazol-1-yl Isovalerate (Compound 4)

Ethyl α-bromoisovalerate (5 g) was added dropwise to a solution of the sodium salt of 1,2,4-triazole [prepared from reacting 1,2,4-triazole (1.8 gm) with sodium hydride (1.26 g; 50% oil dispersion)] in dimethylformamide (30 ml). The reaction mixture was kept at 55°–60° for 5 hours, the solvent removed in vacuo, and the residue extracted with ether; the ethereal layer was then washed with water and dried (sodium sulphate). The solvent was removed in vacuo to leave a residual oil which was distilled, as an oil, to give the title compound.

EXAMPLE 4

α-1,2,4-Triazol-1-yl Caproanilide (Compound 5)

Stage 1

Ethyl α-bromocaproate (4.5 g) in dimethylformamide was added to the sodium salt of 1,2,4-triazole [prepared by reacting 1,2,4-triazole (3 g) with sodium hydride (1.8 g; 50% dispersion in oil)] in dimethylformamide (20 ml). The reaction mixture was maintained at 50° C for 5 hours, the solvent removed in vacuo and the residue extracted with ether (100 ml). The ethereal phase was washed with water (2 × 50 ml) and dried (sodium sulphate), the solvent removed in vacuo and the residue extracted with ether (100 ml). The ethereal phase was washed with water (2 × 50 ml), and dried (sodium sulphate); the solvent was removed in vacuo. Distillation of the residue gave a liquid, b.p. 86°–90°/0.2 mm. To this liquid (12 g) was added potassium hydroxide (6.5 g) in water (50 ml) and the mixture stirred for 15 minutes. The mixture was washed with ether (2 × 20 ml) and then acidified to pH 2 (concentrated hydrochloric acid).

The white solid so obtained was washed with cold water (50 mls) and dried. Recrystallisation of this solid gave α-1,2,4-triazol-1-ylcaproic acid, m.p. 141°–143°.

Stage 2

α-1,2,4-Triazol-1-ylcaproic acid (1.83 g) and thionyl chloride (1.5 ml) were refluxed for 30 minutes. Excess thionyl chloride was removed in vacuo and the resultant gum extracted with methylene chloride (10 ml); the extract was added to aniline (2.83 g) in methylene chloride (10 ml) at 10°–15°. The mixture was stirred for 30 minutes, washed with water (50 ml) and then dried (magnesium sulphate). Removal of the solvent in vacuo gave a solid which on recrystallisation from toluene gave the title compound.

Alternatively this compound can be made starting from α-bromocapranilide as described in Example 1 using the sodium salt of the triazole.

EXAMPLE 5

α-1,2,4-Triazol-1-yl-isovaleroylhydrazine (Compound 11)

Stage 1

To a solution of the sodium salt of 1,2,4-triazole (1.81 g) (prepared as described in Example 4) in dimethylformamide (30 ml) was added ethyl α-bromoisovalerate (5.0 g) dropwise with stirring and the mixture kept at 55°–60° for 5 hours. The bulk of the solvent was removed in vacuo, and the residue was diluted with water and extracted with ether. The ethereal layer was washed with water and dried (magnesium sulphate), and the solvent was distilled off to give α-1,2,4-triazol-1-yl iso-valerate as a clear liquid.

Stage 2

A solution of the above compound and hydrazine hydrate (3 ml) in ethanol (15 ml) was refluxed for 2 hours. Removal of solvent gave a white solid which was recrystallized from ethyl acetate to give the title compound.

EXAMPLE 6

α-p-Chlorobenzyl-α-1,2,4-triazol-1-yl-pinacolone (Compound 10)

α-1,2,4-Triazol-1-yl-pinacolone (3.3 g) in dimethylformamide (20 ml) was added dropwise to a suspension of sodium hydride (0.48 g; 100%) in dimethylformamide (10 ml) at room temperature with stirring. After stirring for 2 hours, p-chlorobenzyl chloride (3.2 g) in dimethylformamide (2–3 ml) was added dropwise and the reaction mixture was kept at 5°–10° for 2 hours. The solvent was removed in vacuo and water was added to the residue. The aqueous solution was extracted with methylene chloride, the organic layer was washed with water and dried (magnesium sulphate). The solvent was removed to give a yellow solid which was crystallised to give the title compound.

EXAMPLE 7

α-1,2,4-Triazole-1-ylcaproamide (Compound 8)

Ethyl α-1,2,4-triazol-1-ylcaproate (3.0 g) was added to liquid ammonia (0.880, 15 ml) and the mixture was shaken well for a few minutes and then left overnight at room temperature. The white solid was filtered and washed with water to give, after recrystallisation from water, the title compound.

EXAMPLE 8

The compounds were tested against a variety of foliar fungal diseases of plants. The technique employed was as follows.

The plants were grown in John Innes Potting Compost (No. 1, or Seed, as appropriate) in 4 cm diameter mini-pots. A layer of fine sand was placed at the bottom of the pot to facilitate uptake of test compound by the roots. Vermiculite was used to cover the seed in the soil tests.

The test compounds were formulated either by bead-milling with aqueous Dispersol T or as a solution in acetone/ethanol which was diluted to the required concentration immediately before use. For the foliage diseases, 100 ppm a.i. suspensions were sprayed on to the foliage and applied to the roots of the same plant via the soil. (Sprays were applied to maximum retention, and root drenches to a final concentration equivalent to approximately 40 ppm a.i./dry soil). Tween 20, to give a final concentration of 0.1%, was added when the sprays were applied to the cereals.

For most of the tests, the test compound was applied to the soil and foliage 1 or 2 days before the plant was inoculated with the diseases. An exception was the test on *Erysiphe graminis,* in which the plants were inoculated 24 hours before treatment. After inoculation, the plants were put into an appropriate environment to allow infection to take place and then incubated until the disease was ready for assessment. The period between inoculation and assessment varied from 3 to 10 days according to the disease and environment.

The disease control was recorded by the following grading:

4 = No disease
3 = 0–5%
2 = 6–25%
1 = 26–60%
0 = >60%

The results are shown in Table II.

TABLE II

| | DISEASE (DAYS BETWEEN INFECTION AND ASSESSMENT) | | | | | |
|---|---|---|---|---|---|---|
| Compound NO | *Puccinia recondita* in wheat (10 days) | *Phytophthora infestans* in tomato (3 days) | *Plasmopara viticola* in vines (7 days) | *Piricularia oryzae* in rice (7 days) | *Botrytis cinerea* in tomatoes (3 days) | *Erysiphe graminis* in barley (7 days) |
| 1 | 0 | 0 | 3 | 0 | 0 | 4 |
| 2 | 0 | 0 | — | 0–1 | 0 | 2–3 |
| 3 | 0 | 0 | 0 | 0 | 0 | 0 |
| 4 | 0 | 0 | 0 | 0 | 0 | 1–3 |
| 5 | 4 | 0 | 0–1 | — | 0 | 4 |
| 6 | 3 | 0 | 0 | 0 | 0 | 4 |
| 7 | 3 | 0 | 0 | 1 | 0–2 | 4 |
| 8 | 0 | 0 | 0 | 0 | 0–2 | 0 |
| 9 | 0 | 0 | 0 | 0 | 0 | 2 |
| 10 | 3 | 0 | 0 | 0 | 3 | 4 |
| 11 | 0 | 0 | 0 | 0 | 0 | 2 |
| 12 | 2–3 | 3 | 0 | 0 | 0 | 4 |
| 13 | 3 | 0 | 0 | 1–2 | 0 | 3–4 |
| 14 | 3–4 | 0 | 0 | 0 | 0 | 4 |
| 15 | 0–3 | 0 | 0 | 0 | 0–1 | 4 |
| 16 | 0 | 1–2 | 0 | 1–2 | 0 | 0 |
| 17 | 2–3 | 3 | 0 | 1–2 | 0 | 4 |
| 18 | 0 | 1 | — | 1 | — | 4 |
| 19 | 4 | 1 | 0 | 0 | 0 | 4 |
| 20 | 3 | 3 | — | 2 | — | 4 |
| 21 | 2 | 3 | — | 1 | 1 | 4 |
| 22 | 2 | 3 | 0 | 1 | 0 | 4 |
| 23 | 0 | 1 | 3 | 0 | 0 | 0 |
| 24 | 0 | 1 | 3 | 3 | 0 | 0 |
| 25 | 0 | 0 | 3 | 0 | 0 | 0 |
| 26 | 0 | 0 | — | 0 | 2 | 3 |
| 27 | 3 | 0 | — | 0–1 | 1 | 4 |
| 28 | 1–2 | — | 1–2 | 0 | 3 | 4 |
| 29 | 4 | 0 | 0 | 0 | 0 | 4 |
| 30 | 4 | 2 | 4 | 0 | 0 | 4 |
| 31 | 4 | — | — | 0–1 | 2–4 | 4 |
| 32 | 2 | 4 | 0 | 1 | 0 | 4 |
| 33 | | 0 | 0 | 0 | 0 | |
| 34 | 3 | 0 | 0 | 0 | 0 | 4 |
| 35 | 3 | 0 | 0 | 1 | 3 | 4 |
| 36 | 1 | 0 | 0 | — | 0 | 4 |
| 37 | 1 | 1 | 0 | — | 0–2 | 3 |
| 38 | 4 | 0 | 1 | — | 0 | 4 |
| 39 | 3 | 0 | 1 | — | 0 | 4 |
| 40 | 4 | 0 | 0 | — | — | 4 |
| 41 | 3 | 0 | 0 | 0 | 2 | 4 |
| 42 | 3 | 0 | 0 | 0 | 3 | 4 |
| 43 | 2 | 0 | 0 | 0 | 0 | 4 |
| 44 | 0 | 0 | 0 | 0 | 2 | 0 |
| 45 | 1 | 0 | 0 | 0 | 0 | 0 |
| 46 | 3 | 0 | 0 | 0 | 0 | 4 |
| 47 | 0 | 2 | 0 | 0 | 2 | 0 |
| 48 | 0 | 0 | 0 | 0 | 3 | 0 |
| 49 | 1 | 0 | 0 | 0 | 3 | 4 |
| 50 | 4 | 0 | 3 | 0 | 0 | 4 |
| 51 | 0 | 0 | 0 | 0 | 0 | 0 |
| 52 | 3 | 1 | 0 | 0 | 1 | 4 |

TABLE II-continued

| | DISEASE (DAYS BETWEEN INFECTION AND ASSESSMENT) | | | | | |
|---|---|---|---|---|---|---|
| Compound NO | Puccinia recondita in wheat (10 days) | Phytophthora infestans in tomato (3 days) | Plasmopara viticola in vines (7 days) | Piricularia oryzae in rice (7 days) | Botrytis cinerea in tomatoes (3 days) | Erysiphe graminis in barley (7 days) |
| 53 | | 0 | 0 | 0 | 1 | 4 |
| 54 | | 0 | 0 | 1 | 0 | 4 |
| 55 | 2-3 | 0 | 0 | 0 | 1-2 | 4 |
| 56 | 0 | 0 | 0 | 0 | 1 | 4 |
| 57 | 3 | — | 0 | 0 | 2 | 4 |
| 61 | 4 | 0 | 0 | 0 | 0 | 4 |
| 62 | 3 | 0 | 0 | 0 | 0 | 4 |
| 63 | 3 | 0 | 0 | 0 | 0 | 4 |
| 64 | 3 | 0 | 0 | 1 | 0 | 4 |
| 65 | 1 | 1 | 0 | 1 | 0 | 4 |
| 66 | 4 | 0 | 0 | 1 | 0 | 4 |
| 67 | 3 | 1 | 0 | 1 | 3 | 4 |
| 68 | 1 | 2 | 0 | 1 | 0 | 4 |

We claim:

1. A method of combating fungal diseases in a plant, said method consisting essentially of the step of applying to the plant, or to the locus of the plant, a fungicidally effective amount of a compound of the formula:

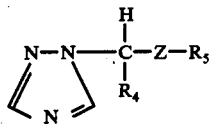

wherein $R_4$ is hydrogen; $C_{1-6}$ alkyl; alkenyl or alkynyl having up to 4 carbon atoms; phenylallyl; phenyl; benzyl or benzyl ring-substituted with halogen, $C_{1-4}$ alkyl or $C_{1-4}$ alkoxy, nitro, trifluoromethyl, cyano or methylenedioxy; α-($C_{1-4}$ alkyl) benzyl or α-($C_{1-4}$ alkyl)benzyl-substituted with halogen; and $R_5$ is hydroxy; $C_{1-6}$ alkoxy; amino; hydrazino, phenylamino or phenylamino ring substituted with $C_{1-4}$ alkyl, halogen, nitro or trifluoromethyl; ($C_{1-6}$ alkyl)amino; phenyloxy or phenyloxy substituted with halogen; benzylamino; benzyloxy; or cycloalkyloxy; and Z is C = O or C = NH, or a fungicidal salt of such a compound.

* * * * *